United States Patent [19]

Plakas

[11] 4,283,490
[45] Aug. 11, 1981

[54] METHOD FOR DETECTION OF LOW LEVEL BACTERIAL CONCENTRATION BY LUMINESCENCE

[76] Inventor: Chris J. Plakas, 8510 Conover Pl., Alexandria, Va. 22308

[21] Appl. No.: 83,758

[22] Filed: Oct. 11, 1979

Related U.S. Application Data

[63] Continuation-in-part of Ser. No. 928,869, Jul. 28, 1978, abandoned, which is a continuation of Ser. No. 764,180, Jan. 31, 1977, Pat. No. 4,144,134.

[51] Int. Cl.$^3$ .................................................. C12Q 1/6
[52] U.S. Cl. .......................................... 435/8; 435/34; 435/291; 435/808
[58] Field of Search ................... 435/8, 34, 36, 37, 38, 435/39, 291, 808

[56] References Cited

U.S. PATENT DOCUMENTS

| | | | |
|---|---|---|---|
| 2,361,261 | 10/1944 | Campbell | 435/808 X |
| 3,520,660 | 7/1970 | Webb | 435/8 X |
| 3,690,832 | 9/1972 | Plakas | 435/291 X |
| 3,940,250 | 2/1976 | Plakas et al. | 435/291 X |
| 4,013,418 | 3/1977 | Plakas | 435/34 X |
| 4,144,134 | 3/1979 | Plakas | 435/8 |

Primary Examiner—Robert J. Warden
Attorney, Agent, or Firm—Quaintance, Murphy & Richardson

[57] ABSTRACT

An improved method for detecting very low concentrations of luminescent reactive molecules from microbial cells in samples of fluids and degraded solids is disclosed. A sample containing microbial cells is treated to eliminate substantially all nonmicrobial material. The microbial cells are then caused to rupture and form a thin film positioned in the vicinity of a photodetector. An appropriate reagent contacts the thin film and the resulting photon emission is observed by the photodetector through an optical filter means which selectively restricts the wavelength of photons which are permitted to pass from the sample to the detector. The strength of the luminescence within the permitted wavelength is measured and recorded as an indication of the concentration of microbial cells in the sample.

3 Claims, 3 Drawing Figures

CALIBRATED CURVES OF MICROBIAL REACTIVE MATERIAL AS COMPARED TO LUMINESCENCE INTENSITY.

METHOD FOR DETECTION OF LOW LEVEL BACTERIAL CONCENTRATION BY LUMINESCENCE

CROSS-REFERENCE TO RELATED APPLICATIONS

This application is a continuation-in-part of my earlier filed, copending application Ser. No. 928,869, filed July 28, 1978 now abandoned, which in turn is a continuation of application Ser. No. 764,180, filed Jan. 31, 1977, now U.S. Pat. No. 4,144,134.

FIELD OF THE INVENTION

The present invention relates to a novel method of determining the presence and concentration of microbial reactive material by bioluminescent or chemiluminescent assay, and more particularly relates to an improved method of determining very low concentrations of reactive material with the aid of selective wavelength optical filters.

DESCRIPTION OF THE PRIOR ART

Current methods employed to determine microbial levels by luminescent assay generally include incubation and extraction of microbial cells in 0.1 to 1 ml volumes of aqueous sample in a cuvette, injection of reagent material into the sample or vice versa, and detection of subsequent luminescence by photodetectors. When the sample contains microbial and non-microbial cells, the method of detecting microbial cells becomes more complicated.

The most serious deficiency of all volume reaction systems is that they lack sensitivity, as these methods can only detect reactive material equivalent to that contained in about $10^4$ microbial cells per assay of 0.1 ml. The term sensitivity is used herein to refer to the ability of a technique or apparatus to detect small amounts of reactive material contained in a test sample. The cause of the limited sensitivity of the test tube technique has never been adequately explained by researchers or instrument manufacturers. It has been established that the luminescence emitted from reactive material contained in 10,000 cells (E. coli) is equivalent in most cases to the intensity of the endogenous luminescence of the reagent; therefore, endogenous luminescence of the reagent makes it impossible to register any lower level intensity that may be emitted by reactive material during the reaction process. The design configuration of the test tube technique also causes optical deficiencies due to refraction, optical coupling and photon absorption in liquid samples. Researchers have attempted to reduce the endogenous luminescence by storing reagent for long periods of time and by other techniques, but have not been able to maintain the reagent's activity. Presently the sensitivity of the test tube technique remains limited because of this reaction configuration and the endogenous luminescence of the reagent. An example of a volume reaction system is disclosed in Chappelle et al, U.S. Pat. No. 3,745,090.

My own prior U.S. Pat. Nos. 3,690,832, 3,940,250, 4,013,418 and 4,144,134 disclose apparatus for the detection of reactive material from cells by luminescent reaction confined to a thin film. This thin film technique has the advantage of assuring adequate oxygen supply needed for the luminescent reaction and decreases significantly the opportunity for optical coupling, refraction, and photon absorption in the sample which would decrease the system sensitivity. Despite this improved configuration, the sensitivity limits imposed by the background emission of photons by the reagents during the reaction remains.

SUMMARY OF THE INVENTION

The present invention overcomes these problems of the prior art devices and methods by providing a method and apparatus for detecting microbial reactive material in a sample by luminescence at microbial concentration levels below that at which the luminescence emitted by the reagents themselves (i.e., endogenous light) exceeds the luminescence emitted by interaction of the reactive material and the reagent. The present invention is the result of my recent observation that the wavelength of endogenous luminescence is principally less than 400 nanometers (300–350) while the wavelength of the luminescence emitted by reaction of reagent with various reactive materials is more predominant at wavelengths greater than 400 nanometers (i.e. 500–550). The quantum efficiency of most photomultiplier tubes currently available is 15% at 350 nm and 2 to 4% at 550 nm. The absolute sensitivity of the photomultiplier tube is about 80% at 350 nm and 15% at 550 nm. The number of photoelectrons emitted by the photocathode per incident photon from endogenous luminescence is therefore many times higher than those emitted by incident photons from luminescence of the reaction with reactive material.

In the present invention, only a selected portion of luminescent emission spectra is observed to establish the strength of luminescence within the permitted wavelength during the reaction between the sample and reagent. The strength of the luminescence can then be interpreted as a cell population by reference to an established calibration curve. By selecting an appropriate spectral range, the presence and even concentration of particular classes of reactant molecules, such as cytochromes, can be established. The observations are preferably conducted with the thin film techniques previously disclosed in my earlier patents with the addition of an appropriate optical filter means being situated between the reaction and the photomultiplier or other optical means.

DESCRIPTION OF THE PREFERRED EMBODIMENTS

Figure 1:
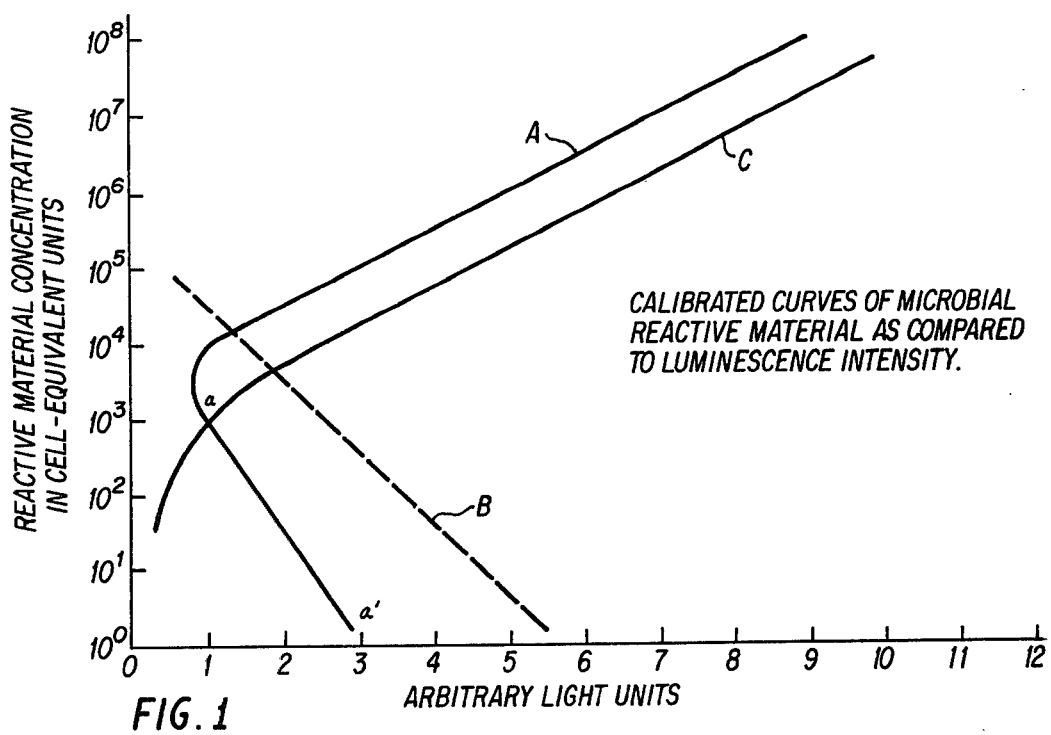
FIG. 1 shows the relationship between luminscence intensity and microbial concentration for samples of E. coli with and without optical filter means being employed.

The presence of a relatively small number of microbial cells in a sample comprising mostly non-microbial material may be detected by treating the sample in the manner previously taught by my earlier patents. The sample treatment consists generally of breaking down any materials present in the sample which are not necessary to the luminescent assay, and filtering and rinsing the sample to eliminate all non-necessary materials. Optimally what remains on the filter is simply the microbial cells with a very minor amount of liquid residue from the rinsing operation. The cell walls of the microbial cells are then ruptured to extract the microbial reactive material contained therein, preferably retaining the microbial reactive material as a substantially undiluted residue on the surface. A luminescence-causing reagent is then introduced in amount sufficient to saturate the extracted microbial reactive material preferably while it is on the filter surface. This reagent introduction occurs in such a location that detecting and recording an indication of the intensity of the luminescence emitted by the reaction between the reagent and the microbial reactive material can occur.

Selected chemicals and hydrolyzing enzymes are used to degrade solid portions of the sample and release non-microbial reactive material without affecting the microbial cells. A small amount of dioctyl sodium sulfosuccinate, octyl phenoxy polyethoxethanol or any other surfactant is added to the sample to reduce surface and interfacial tension for easy filtration through a membrane filter, usually of 0.45 micron mean pore size. Rinsing liquids are used after filtration if necessary for the removal of non-microbial reactive material. Microbial cells retained on the filter are then ruptured to extract the microbial reactive material. Extraction means are numerous; for example extraction can be achieved by forcing vapors of volatile liquids such as ether or acetone through the filter unit. Non-chemical means of extraction, such as ultrasound and heat may also be used. A heater coil inserted into the outlet plate of the filtration unit extracts cells satisfactorily. The most useful extractants in the present technique are methylene chloride, nitric acid, and dioctyl sodium sulfosuccinate. The amount of liquid extractant used varies from 0.001 to 0.050 ml depending on the size of the area on the filter used for the extraction. For filter areas having diameters between 10 and 20 mm, 0.015 ml of extractant medium is satisfactory. Part of the extraction liquid evaporates from the filter and part of it is absorbed in a few seconds, thus leaving the extracted reactive material substantially undiluted on the filter surface. Reagent is then sprayed or otherwise uniformly applied over the filter surface to saturate the reaction area. The undiluted reactive material combines directly with the reagent for reaction.

For bioluminescent assay, the preferred reagent used is luciferase-luciferin mixture, which may be obtained in lyophilized state from Dupont and other suppliers. The concentration is 0.71 millimoles of luciferin with 100 units luciferase diluted in 0.5 ml of 0.75 ml TRIS buffer with $Mg++$ added. The TRIS buffer can be TRIS-Mg buffer from Fisher Scientific Co., or TRIZMA buffer T3753 from Sigma Co.

For chemiluminescent assay, the preferred reagent is luminol solution with sodium perborate or hydrogen peroxide. Equal parts of luminol solution ($5 \times 10^{-3}$ moles or stronger) and sodium perborate (3.846 grams per liter of $H_2O$) are mixed or enough hydrogen peroxide is added to the luminol solution to make 1% concentration.

When the substantially undiluted microbial reactive material present on the filter surface is mixed with reagent supplied in an amount in excess of that necessary to react with all molecules of the reactive material, the quantum efficiency is approximately one and a direct linear relation is supposed to exist between intensity of emitted light and microbial cell population. Since the filter surface is exposed to the air, and as the reagent progressively spreads to the cover the area carrying reactive material, air is present to supply the oxygen demanded by reacting molecules. The thickness of the reaction layer is from 0.05 to 0.5 mm, which permits adequate oxygen supply to all reaction molecules, and thus a complete reaction occurs.

The linear relation between intensity of emitted light and reactive material concentration (and hence microbial cell population) is illustrated in FIG. 1, curve A. The lowest point of linearity of curve A approximately coincides with the value of endogenous light emitted by the reagent material and depends upon the characteristics of the reagent and its preparation. Approximately 0.05 ml of each of the reagents used in this technique emit luminescence equivalent to the reaction of 500 to 1000 microbial cells (E. coli). While the reagent may be purified to reduce the level of endogenous light, the curve of the reaction changes in slope at whatever may be the level of the endogenous light and continues in a linear fashion to zero concentration, as shown in FIG. 1, curve A.

This phenomenon occurs because the light intensity of the reaction is below the normal intensity of the endogenous light and at the same time there is a reduction in the level of endogenous light due to the neutralization of the reagent by the microbial reactive material in the reaction in the range between zero and the normal endogenous light level. Thus the increase or decrease of microbial reactive material in the range below the normal endogenous light level controls the active amount of the enzyme, which in turn affects the intensity of endogenous light which is used as an indicator of the amount of microbial reactive material involved in the reaction.

Since endogenous luminescence is a function of reagent activity, by progressively deactivating the reagent, the endogenous luminescence is also progressively reduced. If reactive material is used as deactivating agent, the curve of deactivation of the reagent resembles Curve A, section a—a′. If microorganisms carrying reactive material are used as deactivating agent the number of microbial cells can be computed from curve A, a—a′.

Since values of luminescence intensity in concentrations near that of the endogenous light can be double valued (i.e. cross the concentration curve twice), the simple measurement of emitted light intensity from a sample does not give a unique value for microbial cell population. It is, of course, the very object of the procedure to establish the microbial cell population and thus additional steps in procedure are necessary.

In a first preferred method of the present invention, a first measurement of emitted light intensity from a sample is conducted as previously described, but only on a first portion of the sample. A second portion of the sample of a different volume or diluted by a known factor is subjected to the previously described procedure.

The two measurements can then be compared to establish which portion of curve A is appropriate to use to specify the microbial population. A further appreciation of the procedure can be obtained by considering Example which follows.

Figure 2:
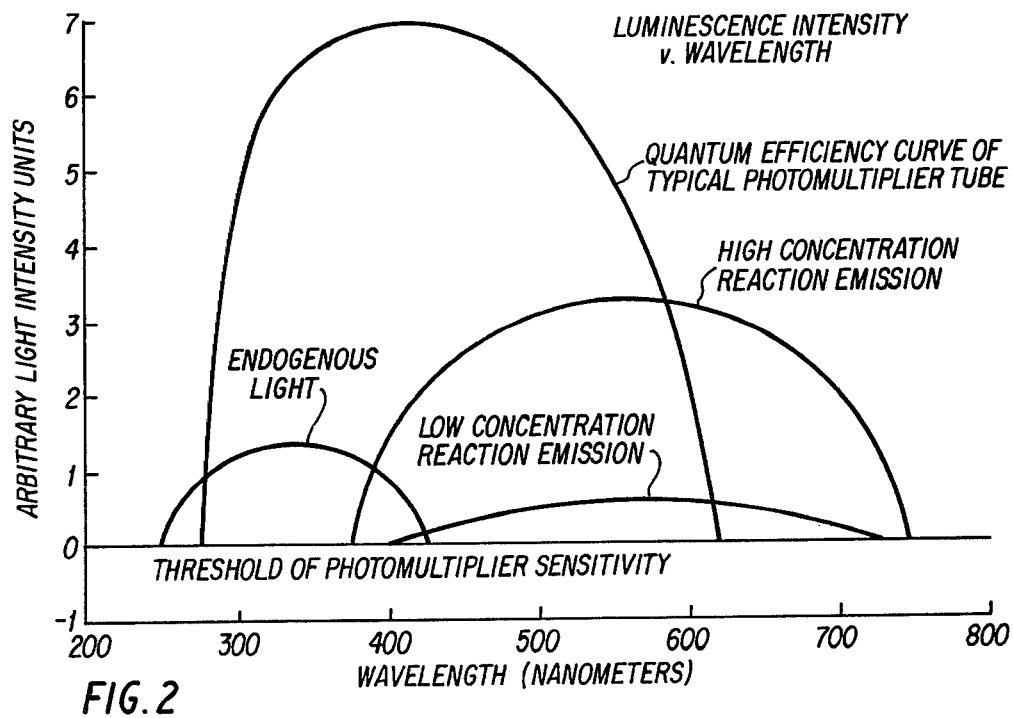
FIG. 2 shows the endogenous and microbial luminescent intensity curves as a function of wavelength.

This requirement of two separate tests to establish microbial population of a single sample while satisfactory is not desirable. As previously mentioned, it has been recently discovered that the intensity of light as a function of wavelength for the endogenous reaction is different from that of the microbial cell material reaction with the reagents as illustrated in FIG. 2. This fact permits the construction of an apparatus capable of uniquely determining microbial cell population in the ambiguous region with a single test in as much as the difference of wave length spectrum between endogenous luminescence of the reagent and luminescence of the reaction is totally responsible for the appearance of the negative slope reaction curve A, part a—a' at lower concentrations.

Recalling that the endogenous luminescence is a function of reagent activity, it can be appreciated that by progressively deactivating the reagent, the endogenous luminescence is also progressively reduced. When the progressive deactivation takes place, the endogenous luminescence of wave length about 350 nm also decreases. The luminescence of the reaction between reagent and reactive material of wave length about 500 nm is emitted concurrently with the endogenous luminescence. As previously indicated, the luminescence of the reaction falls largely outside the most sensitive region of contemporary photodetectors and thus the endogenous luminescence is the dominating activity before the photocathode. As the reactive material increases toward 10,000 units, the endogenous luminescence becomes weaker and the luminescence of the reaction becomes stronger until a balancing point occurs. From this point a and up the reaction curve A reverses and continues linearly.

If an optical filter permitting transmission of only spectrum wavelength above 400 nm, say 500-650 nm, is placed between the reaction and photodetector, the Curve A, will take the shape of Curve C and permit a resolution above 1000 units. If an optical filter permitting transmission of only wave lengths less than 400 nm, say 300-400 nm, is used, the section of the curve a—a' will take the shape of Curve B. The reaction curve B allows the apparatus to detect reaction luminescence levels below the level of endogenous luminescence.

Figure 3:
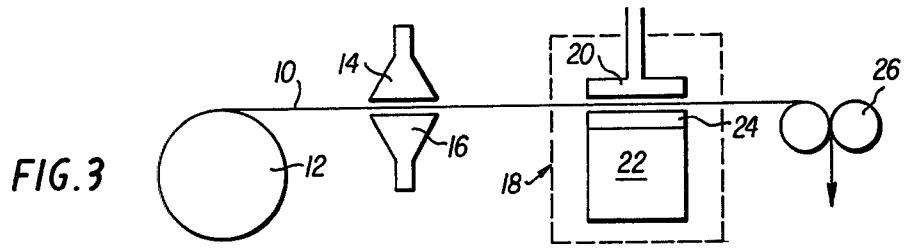
FIG. 3 is a schematic diagram of an apparatus for performing the inventive method.

The optical filter is placed between the reaction and the photodetector in a design configuration that permits filters to be changed rapidly and without interfering with the reaction process. The filter material can be any commercial optical filter made of glass or plastic and cut to correct dimensions. FIG. 3 schematically illustrates an apparatus capable of performing the procedure outlined above. This apparatus can be a modification of that apparatus illustrated in my earlier U.S. Pat. No. 4,013,418 (for example, note FIG. 6 and the discussion relating thereto).

The apparatus can comprise a filter media 10 preferable in the form of a continuous strip supplied from a supply reel 12. A sample is introduced to the filter media 10 between extractors 14 and 16 and then rinsed, filtered, etc., to obtain the substantially undiluted microbial reactive material layer on the filter media. The filter media then is pulled by motor means 26 to a reaction location 18 where the prescribed amount of reagent is applied by applicator 20. The luminescent emission is observed by photodetector 22 through optical filter means 24 and the microbial population established by reference to curves B and C of FIG. 1. Details of the construction of an apparatus for practicing this invention can be obtained by considering my prior U.S. Pat. Nos. 3,690,832, 3,940,250 and 4,013,418 with the addition of an optical filter means as herein described.

The preferred reaction configuration of the preferred embodiments of the invention isolates reactive material from the liquid portion of the sample and directly introduces fluid reagent to saturate and react each molecule of reactive material while the reaction components are spread in a thin layer substantially parallel to the photocathode so that the reacting molecules are viewed at equal distances without refraction losses and thus permitting detection of small luminescent intensities. The application of optical filters in luminescence technique can also provide a new way of identifying the nature of reactive material in addition to detecting it. For example, cythochromes contained in various microbial and nonmicrobial cells can be detected with luminescence technique and by using various optical filters having the wavelength transmission characteristics of a particular luminescent reactive molecule sought to be detected, the exact class can be identified since each class of cythochrome emits a different wave length. Other components not associated with biological samples can also be identified by the luminescence technique using various optical filters for different wave lengths.

The invention is further illustrated by the following examples. These non-limiting examples are illustrative of certain embodiments designed to teach those skilled in the art how to practice the invention and to represent the best mode contemplated for carrying out the invention.

Before the determination of microbial concentration in the sample is carried out, it is necessary to determine the enzyme effectiveness for each lot of enzymes received from the manufacturers. (see Example 2.) The enzyme effectiveness thus determined indicates the necessary enzyme concentration for microbial determination.

Determination by chemiluminescent assay is carried out using luminol solution. Luminol reagent is made by dissolving 0.855 g. of luminol (luminol-5-amino-2,3-dihydro-1,4-phthalazinedione) per 50 ml. of 1.5 N. sodium hydroxide solution (1.5 N NaOH=60 g. NaOH per liter $H_2O$).

Determination by bioluminescent assay is similar to the chemiluminescent assay except that luciferase-luciferin enzyme solution is used instead of the luminol solution described above. Luciferase-luciferin is obtainable from the Dupont Company.

EXAMPLE 1

Milk analysis

Before starting the analysis, the free porphyrins occurring in milk and any traces of iron from milk containers must be eliminated. This is carried out as follows:

For porphyrin elimination: Add 1% by volume of hydrogen peroxide to the milk sample. Allow 2-5 minutes for degradation.

For soluble iron elimination: Add 1 part of EDTA solution to 9 parts of milk. EDTA solution is 16.8 g. ethylenediamine tetra-acetic acid in 250 ml. water.

TRITON X-100 (octyl phenoxy polyethoxyethanol), a surfactant obtainable from the Rohm and Haas Corporation, may be added to the milk sample to facilitate filtration. For a 1 ml. sample of milk, 0.1 ml. of a 1% volume solution of Triton-X is used. Dioctyl sodium sulfosuccinate can also be used as a surfactant.

The analysis of the milk sample is carried out as follows.

(1) The pH of the milk is adjusted to 8 by adding nitric acid to decrease the pH or sodium hydroxide to increase the pH.

(2) To secure bacterial cells which are free of nonbacterial cells (white cells and proteins) contained in the milk, the sample is mixed with Rhozyme 41 protease solution. Rhozyme 41 solution is made as follows: 5 ml. water is added to 1 g. Rhozyme 41 and 12 hours at 10° C. are allowed for complete mixing. The mixture is contrifuged at 12,000 RCF×G and the supernatant liquid is filtered through a 0.2 micron filter. 1 ml. of this Rhozyme protease solution is mixed with a 9 ml. milk sample and 10 minutes are allowed for degrading. The degrading process ruptures the nonbacterial cells. The sample may then be diluted in 4 or 5 parts of water to achieve better filtration.

(3) The sample is then filtered to remove the liquid part of the sample, which contains the former contents of the ruptured nonbacterial cells. The bacterial cells which are not affected by the Rhozyme are retained on the filter. In this filtration, the filter plunger is tightened, and then 1–5 ml. of the degraded and diluted milk sample is forced through the filter unit.

(4) The filter is then flushed with 1–5 ml. of $H_2O$.

(5) Air is then forced through the filter with a plastic syringe to remove all liquid from the filter.

(6) 0.015 ml. of 0.1 $NHNO_3$ extractant is introduced on the filter (for a filter area of 10 mm.) with a 0.05 ml. syringe using a 52 mm. needle length to avoid piercing the filter. One minute is allowed for extraction. This ruptures the bacterial (microbial) cells and exposes reactive bacterial material such as ATP (adenosine triphosphate) and hemoglobin.

(7) The filter tape is moved to the reaction position.

(8) The instrument is adjusted to zero and the photomultiplier shutter opened.

(9) A 0.5 ml. syringe containing 0.04 ml. of luminol reagent is inserted in the reagent port, and pressed carefully until the rubber stopper is pierced. The luminol reagent is injected onto the filter very gently while pressing the button to initiate measurement of the luminescence and thus a determination of the bacterial count.

The procedure as described in Steps (1) to (9) above can be repeated as many times as is necessary with different ratios of enzyme solution to sample in Step (2) above in order to ensure that the luminescence count is within a suitable range for accurate determination on the apparatus. The most suitable ratio of enzyme solution to sample is used for the determination of the microbial count in the samples to be analysed.

EXAMPLE 2

In order to calibrate one lot of luminescence reagent for use in running these tests, a master sample of bacteria such as *E. coli* is grown. By the use of a microscope, the number of bacteria per unit volume in the master sample is determined by counting. The master sample is then diluted with the amount of water which is necessary to generate a standard sample containing $10^{10}$ bacteria per l. of standard sample. One unit of the $10^{10}$ standard sample is withdrawn and combined with nine units of water to make a second standard sample containing $10^9$ bacteria per ml. of standard sample. This process is repeated to make nine additional standard samples of respectively $10^8$, $10^7$, $10^6$, $10^5$, $10^4$, $10^3$, $10^2$, $10^1$, and $10^0$ bacteria per ml. of standard sample. The pH of each standard sample is adjusted to 8. One ml. of the $10^{10}$ standard sample is placed on the filter and steps (5) through (9) as in Example 1 are carried out to calibrate the lot of luminol reagent used in step (9). The test is repeated for four additional one ml. test samples of $10^{10}$ standard sample, and the results of the five tests of the $10^{10}$ standard sample are averaged to obtain a luminescence intensity value for the $10^{10}$ standard sample. This average luminescence intensity value is plotted on a log-log graph of microbial concentration vs. luminescence intensity. The five tests are repeated for each of the ten additional standard samples, and the resulting average values are plotted on the log-log graph. The curve A in FIG. 1 represents the results of the calibration of one such lot of reagent. This calibration curve is used in other tests conducted with the same lot of reagent to assign bacterial count values to various luminescence intensity values.

EXAMPLE 3

In order to arrive at calibration curve C, the procedure of Example 2 is repeated with an optical filter permitting transmission only of photons of wavelength greater than 400 nanometers positioned between the sample and the photomultiplier. This calibration curve can then be used in subsequent tests conducted with the same lot of reagent and with the same optical filter to uniquely assign microbial cell population values to various samples.

EXAMPLE 4

In order to arrive at calibration curve B, the procedure of Example 2 is repeated with an optical filter permitting transmission only of photons of wavelengths less than 400 nanometers positioned between the sample and photomultiplier. This calibration curve can then be used with the same optical filter to uniquely assign microbial cell population values to very low population situations.

EXAMPLE 5

A sample of unknown concentration is tested by placing a 1 ml. sample on a filter surface and carrying out steps (5) through (9) of Example 1, repeating the test four additional times, and averaging a luminescence intensity value of $2.0 \times 10^0$ is obtained in step (9), corresponding to a microbial concentration of either $1.5 \times 10^1$ or $5.0 \times 10^4$ microbes per ml. A second test is run using 2 ml. of the same sample and a luminescence intensity value of $1.7 \times 10^0$ is obtained, thereby indicating that the $1.5 \times 10^1$ concentration value was correct. (Had the second test given a luminescence intensity value of $3.00 \times 10^0$, the $5.0 \times 10^4$ value would have been the correct concentration value.)

EXAMPLE 6

A 1 ml. sample of the sample of Example 5 is placed on the filter tape of the apparatus with the optical filter employed in Example 4 positioned between the filter tape and the photomultiplier and steps (5) through (9) of Example 1 are carried out. The luminescence intensity value of $4.2 \times 10^0$ is obtained in step (9) corresponding to a microbial population of $1.5 \times 10^1$ viewing the calibration curve B.

EXAMPLE 7

A 1 ml. sample of the sample of Example 5 is placed on the filter tape of the apparatus with the optical filter employed in Example 3 positioned between the filter tape and photomultiplier and steps (5) through (9) of Example 1 are carried out. The luminescence intensity value of $1.5 \times 10^0$ is obtained in step (9) corresponding to a microbial population of $2.0 \times 10^3$ viewing the calibration curve C.

EXAMPLE 8

To identify the nature of reactive material in addition to detecting it, an absorbing filter that is specific to the wavelength emitted by the catalyst involved in the reaction is placed between reaction space and photodetector.

A 1 ml. sample from Example 5 is placed on the filter tape of the apparatus. The objective is to determine whether the reaction is caused by cytochrome c or ferric chloride suspected to be present in the sample. One assay is run without filter and one with filter absorbing 550 nm wavelength. The reduction of luminescent intensity with the filter in position indicated that the reaction is a result of cytochrome c. The effect of absorbing filters of wavelengths other than that specified should be tabulated and factored into final results.

In all of the above examples wherein multiple tests are run and averages taken, various statistical techniques can be used. Different numbers of samples can be used, and samples which are quite far from the average can be discarded. Instead of five tests, seven tests could be run, the highest and lowest values discarded, and the remaining values averaged.

What is claimed:

1. An improvement on a method of detecting the presence of microbial luminescent reactive molecules in a sample wherein the concentration of said molecules is so low as to have the luminescent reaction due to said molecules masked by extraneous luminescent reactions of the reagents themselves, the method comprising the steps of:
   (A) placing said sample, wherein the concentration of said molecules is so low as to have the luminescent reaction due to said molecules masked by extraneous luminescent reactions of the reagents themselves, in a designated reactive location,
   (B) situating an optical detector means adjacent the reactive location for detecting photon emission from the sample,
   (C) adding a reagent to the sample in an amount exceeding the minimum necessary to cause luminescence of all the luminescent reactive molecules in the sample, and
   (D) observing the strength of luminescence during the reaction between the sample and reagent with the aid of the optical detector means, the improvement comprising the step of:
   positioning an optical filter means between the optical detector means and the sample for selectively restricting the wavelength of photons which are permitted to pass from the sample to the detector means to those photons having a wavelength less than about 400 nanometers.

2. An improvement on a method of detecting the presence of microbial luminescent reactive molecules in a sample wherein the concentration of said molecules is so low as to have the luminescent reaction due to said molecules masked by extraneous luminescent reactions of the reagents themselves, the method comprising the steps of:
   (A) placing said sample, wherein the concentration of said molecules is so low as to have the luminescent reaction due to said molecules masked by extraneous luminescent reactions of the reagents themselves, in a designated reactive location,
   (B) situating an optical detector means adjacent the reactive location for detecting photon emission from the sample,
   (C) adding a reagent to the sample in an amount exceeding the minimum necessary to cause luminescence of all the luminescent reactive molecules in the sample, and
   (D) observing the strength of luminescence during the reaction between the sample and reagent with the aid of the optical detector means, the improvement comprising the step of:
   positioning an optical filter means between the optical detector means and the sample for selectively restricting the wavelength of photons which are permitted to pass from the sample to the detector means to those photons emanating from said extraneous luminescent reaction of the reagents themselves.

3. The improvement of claim 1 or 2 further comprising the step of comparing the observed strength of luminescence with a previously calibrated curve to establish microbial cell population in the sample.

* * * * *